United States Patent [19]

DiFoggio

[11] Patent Number: 5,114,567
[45] Date of Patent: May 19, 1992

[54] METHOD FOR DETERMINING THE PROPERTIES AND AMOUNT OF FLUID IN A SAMPLE

[75] Inventor: Rocco DiFoggio, Houston, Tex.

[73] Assignee: Shell Oil Company, Houston, Tex.

[21] Appl. No.: 149,758

[22] Filed: Jan. 29, 1988

[51] Int. Cl.$^5$ ............................................. C10G 1/00
[52] U.S. Cl. .................................. 208/401; 208/323; 23/306; 436/29; 436/31
[58] Field of Search ................. 208/401, 323; 23/306, 23/307; 436/29, 31

[56] References Cited

U.S. PATENT DOCUMENTS

| | | | |
|---|---|---|---|
| 2,712,986 | 7/1955 | Huckabay | 436/31 |
| 2,854,396 | 9/1958 | Hunt et al. | 436/31 X |
| 3,847,549 | 11/1974 | Schorno | 208/401 X |

FOREIGN PATENT DOCUMENTS 470591  5/1975  U.S.S.R. ................................ 436/31

OTHER PUBLICATIONS

ASTM Standards, Part 7, 1958, pp. 43-44.

*Primary Examiner*—Anthony McFarlane

[57] ABSTRACT

Methods are provided for determining the amount of fluids in a porous sample and determining petrophysical properties of those fluids. The methods employ a two component azeotropic solvent capable of dissolving both hydrocarbon and aqueous fluids in a porous sample. The methods extract the fluids from the porous sample with a soxhlet extractor using the azeotropic solvent and then separates the two components into a solvent containing hydrocarbon fluids and a solvent containing aqueous fluids. The amounts of these extracted fluids may then be determined and the petrophysical properties of the fluids determined.

11 Claims, 1 Drawing Sheet

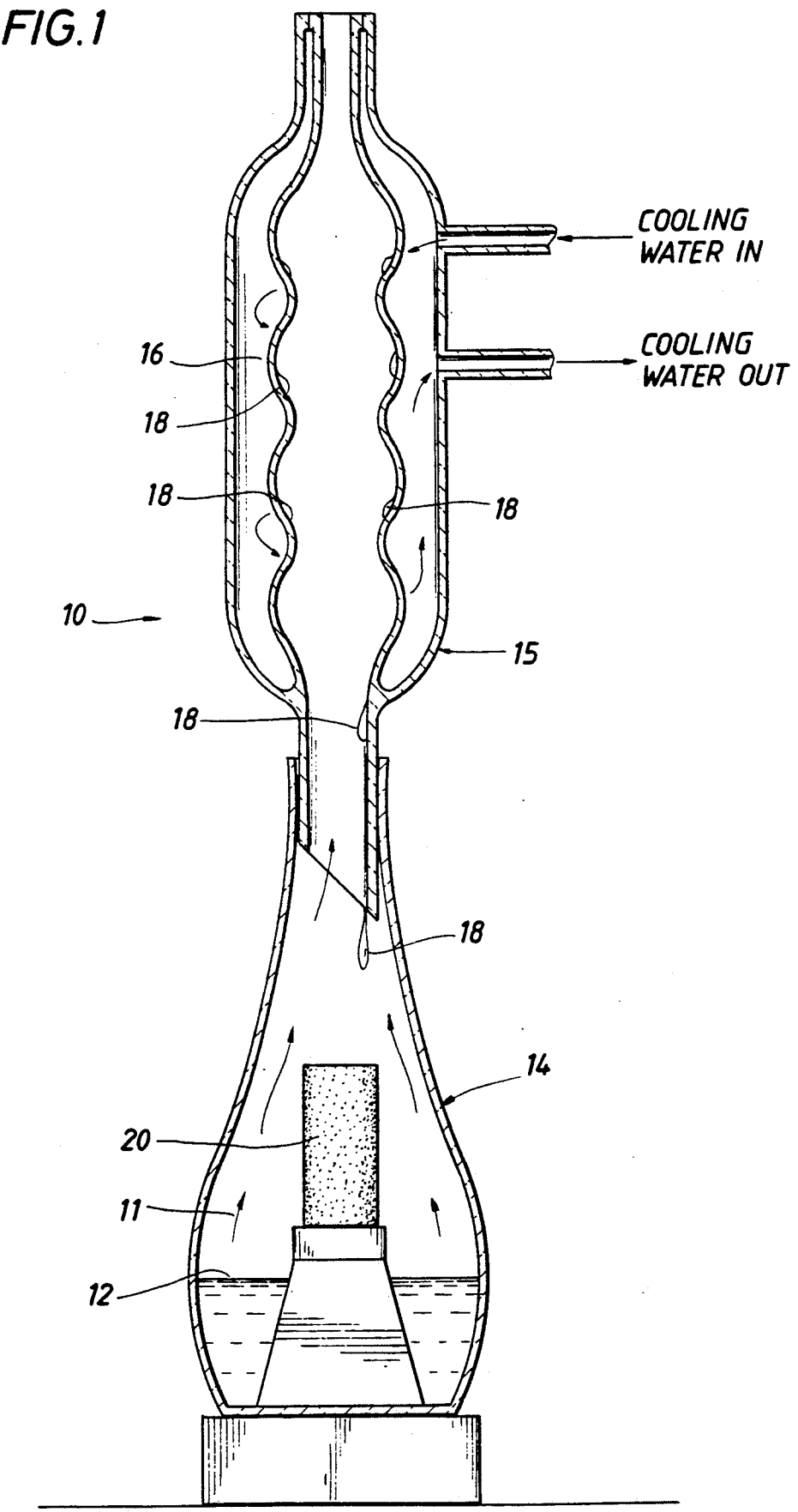

METHOD FOR DETERMINING THE PROPERTIES AND AMOUNT OF FLUID IN A SAMPLE

BACKGROUND OF THE INVENTION

The present invention relates to the exploration and production of petroleum from earth formations, and more particularly, to methods for determining the amount of and properties of fluids present in such a formation.

In the petroleum industry, one of the most valuable and informative techniques for determining the characteristics of an earth formation located well below the surface, and the nature of the fluids which it may contain, is to remove and bring a portion of the formation and/or its fluids to the surface for analysis. This is done most commonly by "coring" the formation. This coring may be accomplished by conventional coring, pressure coring or sponge coring, when it is desired to recover a substantial portion of a formation or formations. However, sidewall plugs or cores are also employed, when only a small portion of the earth formation is desired or when more economical samples are desired.

It is often important to type the hydrocarbon crude in order to be able to determine the ease of removal of the crude oil. A reliable method for estimating key hydrocarbon properties, such as API gravity, or viscosity from sidewall samples could preclude the need for expensive production testing. The potential economics through reduced costs and/or reduced risks to a well could be substantial. Further, variations in hydrocarbon properties within or between reservoirs could be more easily determined with increased sample density at lower cost.

The importance of coring in the production of petroleum has recently been increasing as more and more secondary and tertiary recovery is being made of petroleum reserves. In a formation undergoing primary production, the original reservoir fluids are little altered from their condition for the last several thousand or more years. They may migrate as the oil is produced, but their properties are not changed significantly. However, when fluids and/or other compounds are injected into a formation to stimulate its production, the nature of the connate fluids is accordingly altered, sometimes to a very substantial extent. When this occurs, the more traditional well-logging tools may be unable to provide any useful information about the formation and/or its fluids. In all too many instances, the only way to determine how much oil is left, and thus whether it can be produced economically, is to physically recover a portion of the formation by taking a core sample.

It will therefore be appreciated that the analysis of the amount and properties (viscosity, API gravity, etc.) of the oil in a core sample can be critically important. The viscosity (which is correlated to API gravity) of the crude in a formation often determines whether the oil in the formation may be commercially produced. Similarly, the final true residual oil saturation of a formation is a determination that can make or break a multi-million dollar enhanced recovery project.

Typically, oil is extracted from a portion of a core by means of a soxhlet extractor. Other techniques are also available such as the Dean-Stark extraction technique. However, typically these prior art techniques use a hot solvent which dissolves the oil and boils off the water that is found in the core sample. This is usually the result of using a solvent that is capable of dissolving only the oil and not the water. At the end of the extraction, the oil recovered remains in the solvent and is usually discarded. The soxhlet technique only cleans the sample. In Dean-Stark analysis, the condenser is placed to the side of the extraction vessel's center line and any water that is boiled off is condensed and collected in a side arm under the condenser; the (generally lighter) solvent then floats on top of the collected water and overflows the sidearm to drip back onto the sample. In Dean-Stark analysis the volume of oil is inferred by subtracting the amount of water boiled out of the rock from the total pore volume of the rock. If there was any gas in the original core, the calculated oil volume will be too high. That is, the prior art techniques can not extract and separately recover both the oil and water.

These and other limitations and disadvantages are overcome by the present invention, however, and methods are provided for determining the amount of fluids in a porous sample, and the petrophysical properties of those fluids.

SUMMARY OF THE INVENTION

In a preferred embodiment of the present invention, methods are provided for determining the amount of fluids in a porous sample and determining the petrophysical properties of those respective fluids. The porous sample may be a core sample, sponge core, or cuttings from the drilling process. In particular, the methods of the present invention employ a special two component solvent which is a mixture of two solvents that azeotrope. The mixture is capable of dissolving both the oil and water in a sample. A standard soxhlet extractor is employed to extract the fluids from the sample. The two component solvent and extracts remain in the soxhlet extraction chamber at the bottom of the soxhlet. The mixture of two solvents is then separated into two different solutions to separate the water and its solvent from the oil and its solvent. The oil solvent may then be removed by evaporation from the container leaving a small specimen of extracted crude oil, whose amount may then be determined. The extract may then be characterized by conventional or other testing; for example, the gravity of the extract is preferably determined by concentrating the solution (by boiling off most of the solvent) followed by quantifying the percent by volume of remaining solvent (whose density is known or determined), and then calculating the density of the pure solvent-free oil. Similarly, the amount of water may be determined.

Thus, the oil fluids and the water fluids are both extracted by the two component solvent and then the aqueous and hydrocarbon phases are separated later. The amounts of oil and water fluids from the sample may then be determined. From these samples of water and oil the petrophysical properties of these fluids may be determined by conventional or other means. For example, the viscosity of any hydrocarbons extracted from the sample specimen may be determined by nuclear magnetic resonance while still in solution with the solvent.

Alternatively, the hydrocarbon and solvent solution may be concentrated (by boiling off most of the solvent) followed by determining the percent of solvent remaining, and then measuring the concentrated solution's viscosity directly in a capillary tube. By further concentrating the solution and remeasuring viscosity directly at least one additional time, a viscosity versus percent of solvent relation may be determined which may be extrapolated to a zero percent solvent solution to determine the pure crude's viscosity.

However, for alternative methods of the present invention, the resulting solution of the oil dissolved in solvent (from which the brine or water has been removed) may be analyzed to determine the amount of oil in the solvent and the petrophysical properties of this dissolved oil. That is, following the complete extraction of the oil from the sample, the amount of oil which has been dissolved into its extracting solvent may then be determined.

A method of the present invention, and which produces extremely rapid analytical results, is to compare the solvent solution directly with one or more standard solutions, preferably made up from the particular solvent and oil from the formation, or oil similar thereto to determine the amount of oil in the solvent. The comparison may be by known analytical techniques such as gas chromatography. Also, a set of various dilutions of a similar crude in the particular solvent may be employed with near infrared spectroscopy to determine appropriate spectra to predict the amount of oil in an unknown solution.

It therefore an object of the present invention to provide methods for determining the amounts of fluids in a porous sample, and determining the petrophysical properties of those fluids.

These and other objects and advantages of the present invention will become apparent from the following detailed description, wherein reference is made to figures in the accompanying drawings.

BRIEF DESCRIPTION OF THE DRAWINGS

FIG. 1 is a partial cross-sectional view of a soxhlet extractor for use in accordance with the teachings of the present invention.

DETAILED DESCRIPTION

Referring now to FIG. 1, there may be seen a cross-sectional view of a soxhlet extractor 10 that may be used in accordance with the teachings of the present invention. In particular, the solvent vapors 11 (containing both components of the solvent mixture) are rising from the sample collection 12 and boiling flask 14 at the base of the soxhlet tower assembly 16. These vapors 11 condense on the condenser 16 at the upper portion of the assembly 15 and these condensed vapors 18 drip through or around the porous sample 20.

Further, it may be seen that the glass soxhlet extractor 10 contains at its bottom portion a representative specimen of porous sample 20. Such a porous sample 20 may be a core sample, sponge core, or drilling cuttings. Preferably this sample is a sidewall core plug. This sample is then subjected to the extraction and cleansing action of a solvent in the conventional soxhlet extraction sense. The oil and water fluids in the core specimen are dissolved and extracted by the special two component solvent and are accordingly carried by the solvent mixture to the boiling flask 14 at the bottom of the soxhlet assembly.

The extracted oil, the water, and the solvent mixture will collect in the bottom boiling flask at the bottom of the soxhlet assembly. After extraction, the two components of the solvent may then be separated from each other while retaining their respective oil or aqueous fluids that have been extracted from the sample.

As noted hereinabove, the solvent used to extract the aqueous and hydrocarbon fluids from the core specimen is a special two component solvent. Such two component solvents should employ two components that are miscible with each other and azeotrope with each other, with one capable of dissolving the crude, including asphaltenes, and the other capable of dissolving water. Further, one of these two components must have an affinity for a third liquid to allow for separation of the two components (with one retaining the extracted hydrocarbons and the other retaining the extracted aqueous fluids).

One such two component solvent is a methanol-freon mixture. For example an 8% methanol by weight solvent may be prepared as follows:
3066 gr (~2052 cc) Freon-11 (density 1.497) $CCl_3F$
266.6 gr (~339 cc) Methanol (density 0.7914) $CH_3OH$ Other two component solvents may be made from mixtures of methanol and bromethane, 2-chloropropene, 2-chloropropane, or chloroform; these mixtures from azeotropes with boiling points of 35° C. (5% methanol/95% bromethane), 22° C. (3% methanol/97% chloropropene), 33° (6% methanol/94% chloropropane) and 53° (13% methanol/87% chloroform), respectively. The relatively low boiling point of these mixtures allows their use to extract heat sensitive rocks (such as rock containing gypsum). Further, the higher boiling point mixtures may be extracted at subatmospheric pressure to allow for near room temperature extraction, to avoid damaging heat sensitive rocks.

For those mixtures containing H or C—H bonds the near infrared and NMR methods of determining the amount of and petrophysical properties of fluids extracted by those mixtures may need to be modified to accommodate the presence and influence of these bonds.

Adding more water to a mixture of methanol and Freon-11 "pulls" the methanol out of the two component solution and lets the heavier freon solvent drop to bottom; thus, adding an excess of water to this two component solvent separates the two components, i.e. separates the methanol from the freon.

To illustrate how the amount of aqueous fluid extracted from a sample may be determined, let $F_f$ = volume fraction of freon, $F_m$ = volume fraction of methanol, and $V_B$ = volume of brine in a two component solvent. The brine and methanol are assumed to be floating on top of the freon/crude mixture. Then by adding a known amount of "excess" water, i.e. $V_{AW}$ = volume of added water, the total volume of the aqueous phase, $V_{TAP}$, will be the sum of volumes of the brine, $V_B$, added water, $V_{AW}$, and methanol, $V_m$. Also, let the volume of crude be $V_c$ and the volume of freon be $V_f$. However, a good approximation, (if $V_f \sim V_f + V_c$) is as follows, $$V_B = V_{TAP} - V_m - V_{AW}$$

$$V_B = V_{TAP} - V_F(F_m/F_f) - V_{AW}$$

For example, for a freon-11-methanol mixture $F_m = 0.141$, $F_f = 0.859$, and $$V_B = V_{TAP} - V_F(0.164) - V_{AW}$$

Hydrocarbons that are dissolved in methanol-freon solvent stay in the freon when water is added to separate the methanol from the freon.

For example, the method of the present invention may have the following steps: initially weigh a sample, then place the sample in Soxhlet extractor, and then add 100 ml of the solvent mixture (for example, 80 ml Freon-11, 20 ml Methanol) to the Soxhlet. The sample is then refluxed using a refrigerated condenser. The sample is removed after complete extraction and vacuum dried at room temperature, before it is reweighed and this weight recorded.

To separate the methanol and freon 100 ml of water is added to the Soxhlet flask, which is stoppered and then shaken vigorously to remove all the methanol from the freon.

The Freon is then separated from the methanol/water with a separatory funnel (freon+crude is denser and sinks). The two component solvent is then separated into two separate solutions, one for oil fluids and the other for aqueous fluids. The volume of oil in the oil solution may then be determined by: a refrigerated near-infrared sample holder to get % oil in freon; from NMR; or by boiling off most freon and then measuring the volume of the concentrated solution and percent freon therein. A few microliters may then be injected into a gas chromatograph to get % freon by volume. Some care must be exercised with the freon/hydrocarbon solution, as the freon will evaporate at room temperature. The measured volume of concentration solution, may then be corrected for the amount of solution that is Freon to get volume that is oil. To determine the API gravity of the extracted oil, one may inject one tenth cc of the concentrated solution into Mettler-Parr digital density meter to get the density of the mixture from which the density of the extract $\rho_{crude}$, may be determined as follows, $$\rho_{crude} = (\rho_{mixture} - F_{freon}\, \rho_{freon})/(1 - F_{freon}),$$

where $\rho_{freon}$ is the density of freon and is 1.494 gr/ml for Freon-11, and $\rho_{mixture}$ is the density of the mixture. Similarly, the density of the extract, $\rho_{crude}$ may be determined from, $$\rho_{crude} = (\rho_{mix}) / \left[ 1 - \frac{\frac{\rho_{mix}}{\rho_{freon}} - 1}{\frac{1}{f_{freon}} - 1} \right],$$

where $f_{freon}$ is the fraction of freon solvent by weight in the mixture. Both of these relationships for $\rho_{crude}$ may be generalized for any solvent by replacing the density of freon by the solvent's density. Similar relationships may be derived for API gravity.

Again, to determine the volume of water extracted from rock ($V_{W.E.R.}$), measure total volume of aqueous phase (VAQ) and subtract the known amounts of methanol and added water plus any determined volume of methanol (as a Freon-11/methonol azeotrope—5% methanol by volume) remaining in the rock. ($V_{PV}$=pore volume of the rock.)

$$V_{W.E.R.} = V_{AQ} - 20 \text{ ml (methanol)} - 100 \text{ ml (water)} + 0.05\, V_{PV}$$

Since this involves calculating a small difference between large numbers, it is not as accurate as the oil calculation.

Several different mixtures of crude and freon have been tested to verify these relationships. Crude having a density of 0.9586 gm/ml and an API gravity of 15.98 was mixed by volume with Freon-11 to provide various percentage amounts of freon in the mixture and the density of the mixture measured to determine the crude density from the freon and mixture densities as measured by a Mettler-Parr digital density meter with the following results:

| Freon % of Mixture | Density of Mixture | Calculated Crude Density | Calculated API Gravity |
| --- | --- | --- | --- |
| 5% | 0.9877 | 0.9608 | 15.65 |
| 10% | 1.0155 | 0.9619 | 15.48 |
| 15% | 1.0389 | 0.9627 | 15.35 |
| 20% | 1.0661 | 0.9624 | 15.40 |

The percentage of freon may be determined by gas chromatography, NMR, or near infrared spectroscopy. When the solvent has no C—H bonds, the determination of the amount of crude in solution at high dilutions by near infrared spectroscopy is easier and there is less sensitivity to the type of crude in the unknown solution.

Many other variations and modifications may be made in the techniques hereinbefore described, by those having experience in this technology, without departing from the concepts of the present invention. Accordingly, it should be clearly understood that the method depicted in the accompanying drawings and referred to in the foregoing description are illustrative only and are not intended as limitations on the scope of the present invention.

What is claimed is:

1. A method for determining the amount of hydrocarbon and aqueous fluids in a porous sample, comprising:
   providing a representative specimen of said porous sample,
   extracting hydrocarbon and aqueous fluids from said sample with a solvent mixture comprising a first solvent to dissolve hydrocarbon fluids and a second solvent to dissolve aqueous fluids,
   separating said solvent mixture and extracted fluids into an aqueous containing phase and a hydrocarbon containing phase, and
   determining the amount of hydrocarbon fluid from said separated hydrocarbon containing phase, and the amount of aqueous fluid from said separated aqueous containing phase.

2. A method for determining the petrophysical properties of a crude oil in a porous sample, comprising:
   providing a representative specimen of said porous sample,
   extracting fluids from said sample with a solvent mixture comprising a first solvent to dissolve hydrocarbon fluids and a second solvent to dissolve aqueous fluids,
   separating said solvent mixture and extracted fluids into an aqueous containing phase and a hydrocarbon containing phase, and
   determining the petrophysical properties of said crude oil from said hydrocarbon containing phase.

3. A method as described in claim 1, wherein said solvent mixture comprises an azeotrope.

4. A method as described in claim 1, wherein said solvent mixture comprises halocarbons and methanol.

5. A method for determining the amount of hydrocarbon and aqueous fluid in a porous sample, comprising:

providing a representative specimen of said porous sample, extracting hydrocarbon and aqueous fluids from said sample with a solvent mixture comprising a first solvent to dissolve hydrocarbon fluids and a second solvent to dissolve aqueous fluids, which solvent mixture further comprises halocarbons and methanol, separating said solvent mixture into an aqueous containing phase and a hydrocarbon containing phase by adding an amount of water to said extracted fluids and solvent mixture to form two separate phases, and then using a separatory funnel to separate any aqueous portion from halocarbon portion of said solvent mixture and extracted fluids, and determining the amount of hydrocarbon fluid from said separated hydrocarbon containing phase and the amount of aqueous fluid from said separated aqueous containing phase.

6. A method as described in claim 5, wherein said determining said amount of hydrocarbon fluid step comprises, removing halocarbon from said halocarbon portion and then determining the amount of said hydrocarbon fluid.

7. A method as described in claim 2, wherein said solvent mixture comprises an azeotrope.

8. A method as described in claim 2, wherein said solvent mixture comprises halocarbons and methanol.

9. A method for determining the petrophysical properties of a crude oil in a porous sample, comprising:

providing a representative specimen of said porous sample, extracting fluids from said sample with a solvent mixture comprising a first solvent to dissolve hydrocarbon fluids and a second solvent to dissolve aqueous fluids, separating said solvent mixture into an aqueous containing phase and a hydrocarbon containing phase by adding an amount of water to said extracted fluids and solvent mixture to form two separate phases, and then using a separatory funnel to separate any aqueous containing phase from any hydrocarbon containing phase of said solvent mixture and extracted fluids, and determining the petrophysical properties of said crude oil from said hydrocarbon containing phase.

10. A method as described in claim 9, wherein said determining said properties of said crude oil from said hydrocarbon containing phase step comprises, removing a portion of said first solvent from said hydrocarbon containing phase and then determining the petrophysical properties of said crude oil from said hydrocarbon containing phase.

11. A method as described in claim 9, wherein said determining said petrophysical properties of said crude oil from said hydrocarbon containing phase step comprises, removing a portion of said first solvent from said hydrocarbon containing phase to form a first concentrated solution of hydrocarbon and said first solvent, determining the amount of first solvent in said first concentrated solution and said petrophysical properties of any hydrocarbon fluids in said first concentrated solution, further removing a portion of said first solvent from said first concentrated solution to form a second more concentrated solution, determining the amount of first solvent in said second more concentrated solution and said petrophysical properties of said hydrocarbon fluids in said second concentrated solution, determining a relationship between the amount of first solvent in said first and second concentrated solutions and the petrophysical properties from said first and second concentrated solutions, and then determining from said determined relationship said properties of said crude oil from said properties of said hydrocarbon fluids with no amount of first solvent.

* * * * *